United States Patent
Rosenbaum et al.

(10) Patent No.: US 6,391,404 B1
(45) Date of Patent: May 21, 2002

(54) COEXTRUDED MULTILAYER FILM MATERIALS AND CONTAINERS MADE THEREFROM

(75) Inventors: Larry A. Rosenbaum, Gurnee; Sidney T. Smith, Lake Forest; Steven Giovanetto, Mundelein, all of IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/207,436

(22) Filed: Dec. 8, 1998

Related U.S. Application Data

(63) Continuation-in-part of application No. 08/998,256, filed on Dec. 24, 1997, now Pat. No. 6,024,220, which is a continuation-in-part of application No. 08/478,869, filed on Jun. 7, 1995, now abandoned, which is a continuation-in-part of application No. 09/016,236, filed on Jan. 30, 1998, now Pat. No. 6,083,584.

(51) Int. Cl.$^7$ .......................... B65D 30/02; B65D 30/08; B32B 27/00
(52) U.S. Cl. .................. 428/35.2; 428/35.7; 428/67; 428/476.1; 428/476.9; 428/516; 428/518; 428/519; 383/107; 383/114; 383/119; 383/125; 604/408
(58) Field of Search ................. 428/35.7, 516, 428/518, 35.2, 35.5, 67, 519, 476.1, 476.9; 383/107, 108, 114, 125, 119; 604/408

(56) References Cited

U.S. PATENT DOCUMENTS

| | | |
|---|---|---|
| 2,406,660 A | 8/1946 | Brady |
| 2,422,676 A | 6/1947 | Haman et al. |
| 2,584,633 A | * 2/1952 | Southwick, Jr. ............ 383/107 |
| 2,705,223 A | 3/1955 | Renfrew et al. |
| 2,816,596 A | 12/1957 | Welch |
| 3,062,181 A | 11/1962 | Beguin |
| 3,078,201 A | 2/1963 | Christie |
| 3,255,923 A | 6/1966 | Soto |
| 3,307,549 A | 3/1967 | Zackheim |
| 3,375,300 A | 3/1968 | Ropp |
| 3,390,469 A | 7/1968 | Rader |
| 3,403,064 A | 9/1968 | Bellamy |
| 3,419,654 A | 12/1968 | Chiba et al. |

(List continued on next page.)

FOREIGN PATENT DOCUMENTS

| | | |
|---|---|---|
| AU | A-63709/90 | 11/1991 |
| CH | 649 058 A5 | 4/1985 |
| DE | 14 11 850 A | 10/1968 |
| DE | 24 34 248 A1 | 2/1976 |
| DE | 2800437 | 7/1978 |
| DE | 34 14 199 A | 10/1985 |
| DE | 4142271 | 6/1993 |
| EP | 092897 | 2/1983 |
| EP | 0 092 897 A2 | 11/1983 |
| EP | 148161 | 1/1985 |

(List continued on next page.)

OTHER PUBLICATIONS

Polymer Handbook, 3$^{rd}$. Ed., J. Brandrup and E.H. Immergut, John Wiley & Sons.
Encyclopedia of Polymer Science and Engineering, vol. 16, Styrene, Polymers to Toys, John Wiley & Sons.
Toughened Plastics, C.B. Bucknall, Applied Science Publishers, Ltd.

(List continued on next page.)

Primary Examiner—Rena L. Dye
(74) Attorney, Agent, or Firm—Mark J. Buonaiuto; Joseph A. Fuchs

(57) ABSTRACT

A multilayered film (220) suitable for medical uses is coextruded in a machine direction and comprises a first layer (222) defining a pair of peripheral edges (225,227) extending in a direction parallel to the machine direction. The film has a second layer (224) adhered to the first layer (222). The second layer (224) is positioned within the peripheral edges (225,227) defining a stripe (223).

26 Claims, 5 Drawing Sheets

U.S. PATENT DOCUMENTS

| | | |
|---|---|---|
| 3,485,782 A | 12/1969 | Nagle et al. |
| 3,519,513 A | 7/1970 | Wilharm |
| 3,520,471 A | 7/1970 | Faust |
| 3,551,201 A | 12/1970 | Marchese et al. |
| 3,558,397 A | 1/1971 | Clark |
| 3,570,375 A | 3/1971 | Williams et al. |
| 3,681,138 A | 8/1972 | Ankenbrand et al. |
| 3,768,724 A | 10/1973 | Hill |
| 3,772,136 A | 11/1973 | Workman |
| 3,885,081 A | 5/1975 | Van Paesschen et al. |
| 3,912,843 A | 10/1975 | Brazier |
| 3,937,758 A | 2/1976 | Castagna |
| 3,960,997 A | 6/1976 | Sorensen |
| 3,985,135 A | 10/1976 | Carpenter et al. |
| 3,995,084 A | 11/1976 | Berger et al. |
| 4,005,710 A | 2/1977 | Zeddies et al. |
| 4,022,256 A | 5/1977 | Berkman et al. |
| 4,023,607 A | 5/1977 | Jensen et al. |
| 4,041,103 A | 8/1977 | Davison et al. |
| 4,045,515 A | 8/1977 | Isaka et al. |
| 4,058,647 A | 11/1977 | Inoue et al. |
| 4,072,089 A | 2/1978 | Bosche |
| 4,085,244 A | 4/1978 | Stillman |
| 4,087,587 A | 5/1978 | Shida et al. |
| 4,087,588 A | 5/1978 | Shida et al. |
| 4,095,012 A | 6/1978 | Schirmer |
| 4,103,686 A | 8/1978 | LeFevre |
| 4,112,989 A | 9/1978 | Grode et al. |
| 4,140,162 A | 2/1979 | Gajewski et al. |
| 4,147,827 A | 4/1979 | Breidt, Jr. et al. |
| 4,156,709 A | 5/1979 | Kondo et al. |
| 4,161,362 A | 7/1979 | Blake |
| 4,188,350 A | 2/1980 | Vicik et al. |
| 4,226,822 A | 10/1980 | Yoshikawa et al. |
| 4,227,527 A | 10/1980 | De Frank et al. |
| 4,230,830 A | 10/1980 | Tanny et al. |
| 4,233,367 A | 11/1980 | Ticknor et al. |
| 4,234,026 A | 11/1980 | Bayham |
| 4,244,378 A | 1/1981 | Brignola |
| 4,261,473 A | 4/1981 | Yamada et al. |
| 4,274,900 A | 6/1981 | Mueller et al. |
| 4,286,628 A | 9/1981 | Paradis et al. |
| 4,294,935 A | 10/1981 | Kodera et al. |
| 4,310,017 A | 1/1982 | Raines |
| 4,311,807 A | 1/1982 | McCullough, Jr. et al. |
| 4,322,465 A | 3/1982 | Webster |
| 4,322,480 A | 3/1982 | Tuller et al. |
| 4,324,816 A | 4/1982 | Landis et al. |
| 4,327,726 A | 5/1982 | Kwong et al. |
| 4,332,655 A | 6/1982 | Berejka |
| 4,333,968 A | 6/1982 | Nahmias |
| 4,362,844 A | 12/1982 | Lemstra et al. |
| 4,367,742 A | 1/1983 | Ornstein |
| 4,369,812 A | 1/1983 | Paradis et al. |
| 4,387,184 A | 6/1983 | Coquard et al. |
| 4,405,667 A | 9/1983 | Christensen et al. |
| 4,407,877 A | 10/1983 | Rasmussen |
| 4,407,888 A | 10/1983 | Crofts |
| 4,411,358 A | 10/1983 | Bennwik et al. |
| 4,417,753 A | 11/1983 | Bacehowski et al. |
| 4,421,235 A | 12/1983 | Moriya |
| 4,429,076 A | 1/1984 | Saito et al. |
| 4,432,763 A | 2/1984 | Manschot et al. |
| 4,439,192 A | 3/1984 | Leurink |
| 4,465,487 A | 8/1984 | Nakamura et al. |
| 4,478,858 A | 10/1984 | Baird et al. |
| 4,479,989 A | 10/1984 | Mahal |
| 4,497,857 A | 2/1985 | Bonis |
| 4,507,123 A | 3/1985 | Yoshida |
| 4,514,499 A | 4/1985 | Noll |
| 4,516,977 A | 5/1985 | Herbert |
| 4,521,437 A | 6/1985 | Storms |
| 4,531,997 A | 7/1985 | Johnston |
| 4,540,537 A | 9/1985 | Kamp |
| 4,546,085 A | 10/1985 | Johansson et al. |
| 4,548,348 A | 10/1985 | Clements |
| 4,562,118 A | 12/1985 | Maruhashi et al. |
| 4,568,333 A | 2/1986 | Sawyer et al. |
| 4,568,723 A | 2/1986 | Lu |
| 4,572,854 A | 2/1986 | Dallmann et al. |
| 4,588,648 A | 5/1986 | Krueger et al. |
| 4,599,276 A | 7/1986 | Martini |
| D285,725 S | 9/1986 | Franchere |
| 4,614,781 A | 9/1986 | Hori et al. |
| 4,621,014 A | 11/1986 | Lu |
| 4,627,844 A | 12/1986 | Schmitt |
| 4,636,412 A | 1/1987 | Field |
| 4,640,870 A | 2/1987 | Akazawa et al. |
| 4,641,362 A | 2/1987 | Muller |
| 4,643,926 A | 2/1987 | Mueller |
| 4,650,452 A | 3/1987 | Jensen |
| 4,654,240 A | 3/1987 | Johnston |
| 4,658,433 A | 4/1987 | Savicki |
| 4,678,713 A | 7/1987 | Lancaster et al. |
| 4,680,208 A | 7/1987 | Aoki et al. |
| 4,683,916 A | 8/1987 | Raines |
| 4,684,364 A | 8/1987 | Sawyer et al. |
| 4,686,125 A | 8/1987 | Johnston et al. |
| 4,690,915 A | 9/1987 | Rosenberg |
| 4,692,361 A | 9/1987 | Johnston et al. |
| 4,705,708 A | 11/1987 | Briggs et al. |
| 4,707,389 A | 11/1987 | Ward |
| 4,717,668 A | 1/1988 | Keilman et al. |
| 4,722,725 A | 2/1988 | Sawyer et al. |
| 4,724,028 A | 2/1988 | Zabielski et al. |
| 4,724,961 A | 2/1988 | Shimoyamada et al. |
| 4,726,997 A | 2/1988 | Mueller et al. |
| 4,732,795 A | 3/1988 | Ohya et al. |
| 4,734,327 A | 3/1988 | Vicik |
| 4,735,855 A | 4/1988 | Wofford et al. |
| 4,740,582 A | 4/1988 | Coquard et al. |
| 4,753,222 A | 6/1988 | Morishita |
| 4,760,114 A | 7/1988 | Haaf et al. |
| 4,764,404 A | 8/1988 | Genske et al. |
| 4,767,651 A | 8/1988 | Starczewski et al. |
| 4,770,856 A | 9/1988 | Uthemann et al. |
| 4,772,497 A | 9/1988 | Maasola |
| 4,778,697 A | 10/1988 | Genske et al. |
| 4,792,488 A | 12/1988 | Schirmer |
| 4,795,782 A | 1/1989 | Lutz et al. |
| 4,798,288 A | 1/1989 | Holzner |
| 4,800,129 A | 1/1989 | Deak |
| 4,801,484 A | 1/1989 | Yao et al. |
| 4,803,102 A | 2/1989 | Rainere et al. |
| 4,824,720 A | 4/1989 | Malone |
| 4,829,002 A | 5/1989 | Pattillo et al. |
| 4,834,755 A | 5/1989 | Silverstrini et al. |
| 4,839,292 A | 6/1989 | Cremonese |
| 4,855,356 A | 8/1989 | Holub et al. |
| 4,856,259 A | 8/1989 | Woo et al. |
| 4,856,260 A | 8/1989 | Woo et al. |
| 4,863,996 A | 9/1989 | Nakazima et al. |
| 4,871,799 A | 10/1989 | Kobayashi et al. |
| 4,873,287 A | 10/1989 | Holub et al. |
| 4,876,788 A | 10/1989 | Steer et al. |
| 4,877,682 A | 10/1989 | Sauers et al. |
| 4,885,119 A | 12/1989 | Mueller et al. |
| 4,910,085 A | 3/1990 | Raniere et al. |
| 4,910,147 A | 3/1990 | Bacheowski et al. |

| | | | | | |
|---|---|---|---|---|---|
| 4,915,893 A | 4/1990 | Gogolewski et al. | 5,238,997 A | 8/1993 | Bauer et al. |
| 4,923,470 A | 5/1990 | Dumican | 5,244,971 A | 9/1993 | Jean-Marc |
| 4,927,647 A | 5/1990 | Bailey | 5,254,074 A | 10/1993 | Landers et al. |
| 4,929,479 A | 5/1990 | Shishido et al. | 5,258,230 A | 11/1993 | LaFleur et al. |
| 4,937,194 A | 6/1990 | Pattillo et al. | 5,259,844 A | 11/1993 | Bilstad et al. |
| 4,939,151 A | 7/1990 | Bacehowski et al. | 5,272,084 A | 12/1993 | O'Connell et al. |
| 4,948,643 A | 8/1990 | Mueller | 5,278,231 A | 1/1994 | Chundury |
| 4,957,966 A | 9/1990 | Nishio et al. | 5,287,961 A | 2/1994 | Herran |
| 4,957,967 A | 9/1990 | Mizuno et al. | 5,288,531 A | 2/1994 | Falla et al. |
| 4,966,795 A | 10/1990 | Genske et al. | 5,288,799 A | 2/1994 | Schmid et al. |
| 4,968,624 A | 11/1990 | Bacehowski et al. | 5,290,856 A | 3/1994 | Okamoto et al. |
| 4,976,707 A | 12/1990 | Bodicky et al. | 5,298,300 A | 3/1994 | Hosoi et al. |
| 4,977,213 A | 12/1990 | Giroud-Abel et al. | 5,306,269 A | 4/1994 | Lewis et al. |
| 4,978,579 A | 12/1990 | Rosenbaum | 5,306,541 A | 4/1994 | Bayer |
| 4,994,056 A | 2/1991 | Ikeda | 5,310,676 A | 5/1994 | Johansson et al. |
| 4,996,054 A | 2/1991 | Pietsch et al. | 5,312,867 A | 5/1994 | Mitsuno et al. |
| 4,999,254 A | 3/1991 | Ofstein | 5,317,059 A | 5/1994 | Chundury et al. |
| 4,999,297 A | 3/1991 | Minoura et al. | 5,318,556 A | 6/1994 | Avallone et al. |
| 5,002,623 A | 3/1991 | Steer et al. | 5,334,180 A | 8/1994 | Adolf et al. |
| 5,006,114 A | 4/1991 | Rogers et al. | 5,342,345 A | 8/1994 | Spencer |
| 5,006,601 A | 4/1991 | Lutz et al. | 5,342,886 A | 8/1994 | Glotin et al. |
| 5,017,490 A | 5/1991 | Taiariol et al. | 5,348,525 A | 9/1994 | Buchanan |
| 5,017,652 A | 5/1991 | Abe et al. | 5,348,794 A | 9/1994 | Takahashi et al. |
| 5,034,457 A | 7/1991 | Serini et al. | 5,356,676 A | 10/1994 | von Widdern et al. |
| 5,034,458 A | 7/1991 | Serini et al. | 5,356,709 A | 10/1994 | Woo et al. |
| 5,053,457 A | 10/1991 | Lee | 5,371,141 A | 12/1994 | Gelles et al. |
| 5,062,569 A | 11/1991 | Hekal | 5,378,543 A | 1/1995 | Murata et al. |
| 5,066,290 A | 11/1991 | Measells et al. | 5,378,800 A | 1/1995 | Mok et al. |
| 5,071,686 A | 12/1991 | Genske et al. | 5,387,645 A | 2/1995 | Montag et al. |
| 5,071,911 A | 12/1991 | Furuta et al. | 5,423,421 A | 6/1995 | Inoue et al. |
| 5,071,912 A | 12/1991 | Furuta et al. | 5,437,474 A | 8/1995 | Ament |
| 5,075,376 A | 12/1991 | Furuta et al. | 5,439,454 A | 8/1995 | Lo et al. |
| 5,079,295 A | 1/1992 | Furuta et al. | 5,451,437 A | 9/1995 | Insley et al. |
| 5,085,649 A | 2/1992 | Flynn | 5,464,107 A | 11/1995 | Koeniger |
| 5,088,994 A | 2/1992 | Porat et al. | 5,501,887 A | 3/1996 | Tanaka et al. |
| 5,093,164 A | 3/1992 | Bauer et al. | 5,545,419 A * | 8/1996 | Brady et al. ................ 383/109 |
| 5,093,194 A | 3/1992 | Touhsaent et al. | 5,678,732 A | 10/1997 | Gianpaolo |
| 5,094,921 A | 3/1992 | Itamura et al. | 5,686,527 A | 11/1997 | Laurin et al. |
| 5,098,202 A | 3/1992 | Rosenbaum | 5,733,619 A * | 3/1998 | Patel et al. ............... 428/36.91 |
| 5,108,844 A | 4/1992 | Blemberg et al. | 5,786,010 A | 7/1998 | Yannuzi, Jr. |
| 5,110,642 A | 5/1992 | Genske | 5,910,138 A | 6/1999 | Sperko et al. |
| 5,116,906 A | 5/1992 | Mitzuno et al. | 5,935,847 A * | 8/1999 | Smith et al. ................ 383/109 |
| 5,126,132 A | 6/1992 | Rosenberg | 6,024,220 A * | 2/2000 | Smith et al. ................ 383/107 |
| 5,127,904 A | 7/1992 | Loo et al. | 6,083,587 A * | 7/2000 | Smith et al. ................ 428/518 |
| 5,129,894 A | 7/1992 | Sommermeyer et al. | | | |
| 5,132,363 A | 7/1992 | Furuta et al. | | | |

FOREIGN PATENT DOCUMENTS

| | | |
|---|---|---|
| 5,135,785 A | 8/1992 | Millon |
| 5,139,831 A | 8/1992 | Mueller |
| 5,139,946 A | 8/1992 | Howell et al. |
| 5,145,731 A | 9/1992 | Lund et al. |
| 5,154,979 A | 10/1992 | Kerschbaumer et al. |
| 5,158,499 A | 10/1992 | Guckenberger |
| 5,159,004 A | 10/1992 | Furuta et al. |
| 5,164,267 A | 11/1992 | D'Heur et al. |
| 5,164,268 A | 11/1992 | Dollinger et al. |
| 5,176,634 A | 1/1993 | Smith et al. |
| 5,176,956 A | 1/1993 | Jevne et al. |
| 5,183,706 A | 2/1993 | Bekele |
| 5,185,189 A | 2/1993 | Stenger et al. |
| 5,189,091 A | 2/1993 | Laughner |
| 5,194,316 A | 3/1993 | Horner et al. |
| 5,196,254 A | 3/1993 | Akiyama |
| 5,205,650 A | 4/1993 | Rasmussen |
| 5,206,290 A | 4/1993 | Mizuno et al. |
| 5,209,573 A | 5/1993 | Freeman |
| 5,212,238 A | 5/1993 | Scheibelhoffer et al. |
| 5,218,048 A | 6/1993 | Abe et al. |
| 5,225,346 A | 7/1993 | Matsumiya et al. |
| 5,226,564 A | 7/1993 | Steer et al. |
| 5,230,934 A | 7/1993 | Sakano et al. |
| 5,230,935 A | 7/1993 | Delimoy et al. |

| | | |
|---|---|---|
| EP | 0 148 161 A2 | 7/1985 |
| EP | 310143 | 7/1985 |
| EP | 340305 | 1/1988 |
| EP | 0 310 143 A1 | 4/1989 |
| EP | 446505 | 3/1990 |
| EP | 0 194 684 B1 | 3/1991 |
| EP | 0 446 505 A1 | 9/1991 |
| EP | 488544 | 11/1991 |
| EP | 0 488 544 A1 | 6/1992 |
| EP | 0 491 380 A2 | 6/1992 |
| EP | 552412 | 9/1992 |
| EP | 0 539 800 A3 | 5/1993 |
| EP | 0 539 800 A2 | 5/1993 |
| EP | 0 552 412 A1 | 7/1993 |
| EP | 0 589 575 A1 | 3/1994 |
| EP | 0 675 053 A1 | 10/1995 |
| FR | 2 587 935 A | 4/1987 |
| FR | 2688511 | 3/1992 |
| GB | 623 736 A | 5/1949 |
| GB | 1059554 | 2/1967 |
| GB | 1 465 963 A | 3/1977 |
| GB | 2094832 | 3/1982 |
| GB | 2177974 | 2/1987 |
| GB | 2 177 974 A | 2/1987 |
| JP | 57 034 953 A | 2/1982 |

| | | |
|---|---|---|
| JP | 01 055226 | 3/1989 |
| JP | 1291171 | 11/1989 |
| JP | 3065177 A | 3/1991 |
| WO | WO 83/00158 | 1/1983 |
| WO | 86/07010 | 4/1986 |
| WO | WO 90/03427 | 4/1990 |
| WO | WO 91/09719 | 7/1991 |
| WO | WO 92/14600 | 9/1992 |
| WO | WO 93/02859 | 2/1993 |
| WO | WO 93/09718 | 5/1993 |
| WO | WO 93/23093 | 11/1993 |
| WO | WO 96/09233 | 3/1996 |

OTHER PUBLICATIONS

Polymer Blends, vol. 1, Seymour Newman, Academic Press.

Thermoplastics for Health–Care Products: Clear Choices Are Not So Clear, K.Z. Hong, Ph.D., Baxter Healthcare Corporation.

Plastics Engineering, Oct. 1995, Official Publication of The Society of Plastics Engineers (Wigotsky, Victor, *Medical Plastics*, pp. 18–22).

* cited by examiner

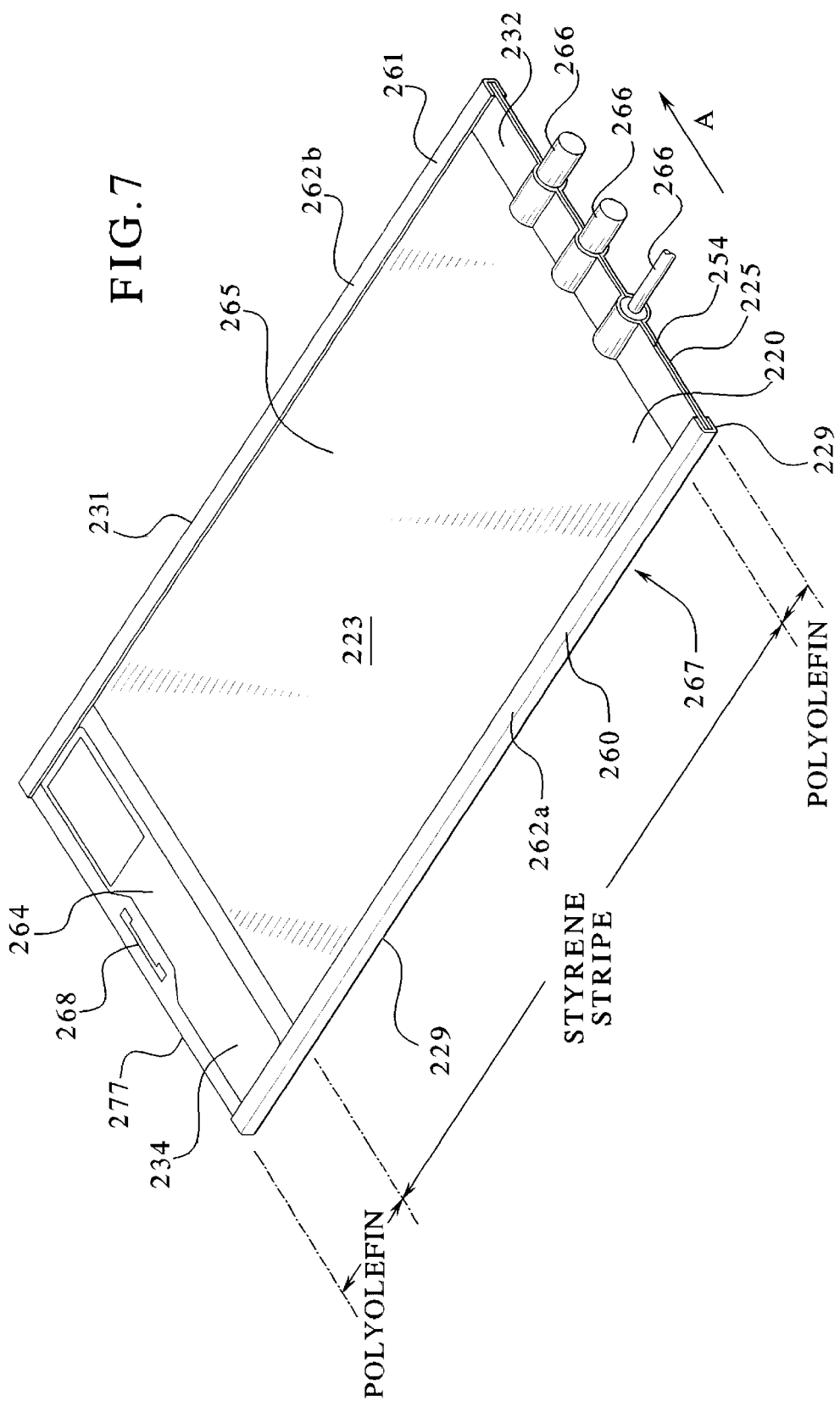

COEXTRUDED MULTILAYER FILM MATERIALS AND CONTAINERS MADE THEREFROM

RELATED APPLICATIONS

The present Application is a continuation-in-part application of U.S. patent application Ser. No. 08/998,256, now U.S. Pat. No. 6,024,220, filed on Dec. 24, 1997 entitled "Encapsulated Seam For Multilayer Materials" (which is a continuation-in-part of U.S. patent application Ser. No. 08/478,869, filed Jun. 7, 1995 now abandoned) and U.S. patent application Ser. No. 09/016,236, now U.S. Pat. No. 6,083,584 filed on Jan. 30, 1998, entitled "Perimeter Seals For Multi-Layer Materials And Method," which Applications are expressly incorporated herein by reference and made a part hereof.

TECHNICAL FIELD

The present invention relates generally to coextruded multilayer film materials and more particularly to containers made from the multilayer film materials.

BACKGROUND OF THE INVENTION

Containers used for the shipping, storing, and delivery of liquids, such as medical or therapeutic fluids, are often fabricated from single-ply or multi-ply polymeric materials. Two sheets of these materials are placed in overlapping relationship and the overlapping sheets are bonded at the inner surfaces of their outer peripheries to define a chamber or pouch for containing liquids. It is also possible to extrude these materials as a tube and to seal longitudinally spaced portions of the tube to define chambers between two adjacent seals. Typically, the materials are joined along their inner surfaces using bonding techniques such as heat sealing, radio-frequency sealing, thermal transfer welding, adhesive sealing, solvent bonding, sonic sealing, and laser welding.

For most applications, the seal formed must be of sufficient strength to withstand the stresses generated by transporting, dropping, or agitating the liquid-filled container. Problems have been encountered with certain materials that do not bond well with themselves or other materials. Problems have also been encountered in forming strong seals in containers having sidewalls made of a layered material. If seals of sufficient strength cannot be formed, this alone could prevent the container from ever reaching the marketplace.

Thus, to achieve a reliable, consistent seal of sufficient strength using any of the above-mentioned bonding techniques, the sealing faces of the film materials must be compatible. In the case of multilayered film materials formed by coextrusion, it also requires that the coextruded film have a high degree of resistance to delamination between the layers, i.e., that each layer be compatible with every layer it contacts. The compatibility requirement places a practical limitation on the products that can be manufactured and, therefore, limits design options. The compatibility requirement also presents problems in attaching other features to the film materials such as when attaching access ports, tail seals or tail hangers to containers constructed from the multilayer films.

There are many applications, however, where using incompatible materials would be desirable if the materials could be reliably bonded into a container in a cost effective manufacturing operation. For instance, applications utilizing coextruded multilayered films have the need for such a material structure. A flexible container could then be manufactured from multilayered films wherein the outer layers of the films allow for bonding strong peripheral seams while the inner layers of the films provide for specific functionalities, such as cell culture surfaces and inert surfaces to certain pharmacological agents.

Problems have been encountered in sealing containers wherein the container walls are multilayered and wherein the inner layers are made from polystyrene. The bond formed between the polystyrene layers is not sufficiently strong to withstand the hydraulic shock generated by container fluids. In one such example, a cell culture container described in co-pending and commonly assigned U.S. patent application Ser. No. 08/330,717, now U.S. Pat. No. 6,297,046, is constructed of a multilayered material having an outer layer of a polymer blend of styrene-ethylene-butene-styrene ("SEBS") block copolymer (40%–85% by weight), ethylene vinyl acetate (0–40% by weight), and polypropylene (10%–40% by weight) and an inner layer of a polystyrene. It was found that only weak seams could be achieved by sealing or bonding the polystyrene layers to one another. The seams were considered "fragile," and the container was not sufficiently robust enough to tolerate normal handling procedures. Also, the resulting filled cell culture container was not capable in many instances of being dropped at heights above six feet without seal failure.

Copending and commonly assigned U.S. patent application Ser. No. 08/998,256, now U.S. Pat. No. 6,083,584, discloses an improved seal construction for the cell culture container by encapsulating the peripheral margins of the film materials as opposed to joining the inner facing surfaces of the films as conventional methods do. By bonding the peripheral margins through encapsulation, the container can withstand elevated mechanical stresses. Encapsulation, however, can be a time-consuming and intricate procedure, especially when it is necessary to encapsulate three or four sides of a container.

Due to the problems relative to sealing containers manufactured from multilayered materials, there is a need for creating a multilayered material that is capable of forming a suitably strong peripheral seal when the multilayered film is formed into a container.

SUMMARY OF THE INVENTION

The present invention relates to multilayered films and containers made from the films.

In a first aspect of the present invention, a multilayered film suitable for medical uses is provided that is coextruded in a machine direction. The film has a first layer defining a pair of peripheral edges extending in a direction parallel to the machine direction. The film also has a second layer adhered to the first layer, wherein the second layer is positioned within the peripheral edges to define a stripe.

According to another aspect of the invention, the film has a width and a thickness wherein the thickness of the film is substantially uniform across the width of the film.

According to a further aspect of the invention, the first layer of the film is composed of a polyolefin, and the second layer of the film is composed of a polystyrene.

According to yet another aspect of the invention, the first layer of the film has a first flange and a second flange. The flanges extend in a lateral direction wherein the second layer is positioned between the flanges. The first layer also has a channel positioned between the flanges and extending parallel to the flanges wherein the second layer is positioned in the channel. The thickness of the film is substantially uniform across the width of the film.

According to a further aspect of the invention, the second layer is positioned in the channel and defines an overlap area. The second layer has a thickness of 0.0003 in. to 0.003 in. The first layer has a thickness of 0.006 in. to 0.012 in. at the flanges and a thickness of 0.0057 in. to 0.009 in. at the overlap area.

According to another aspect of the invention, the second layer of the film defines an inner cell growth surface.

According to a further aspect of the invention, when the film is viewed from a direction perpendicular to the machine direction, the film is noncontinuous by having a first layer section adjacent the stripe of the second layer adjacent another first layer section.

According to yet a further aspect of the invention, the second layer has a first longitudinal portion removed to defme a first longitudinal segment on the first layer, and the second layer has a second longitudinal portion removed to define a second longitudinal segment on the first layer.

According to another aspect of the invention, a container suitable for medical uses is constructed from the film.

Other advantages and aspects of the present invention will become apparent upon reading the following description of the drawings and detailed description of the invention.

BRIEF DESCRIPTION OF THE DRAWINGS

FIG. 7 is a perspective view of a container constructed of multilayer films of the present invention;

DETAILED DESCRIPTION

Figure 1:
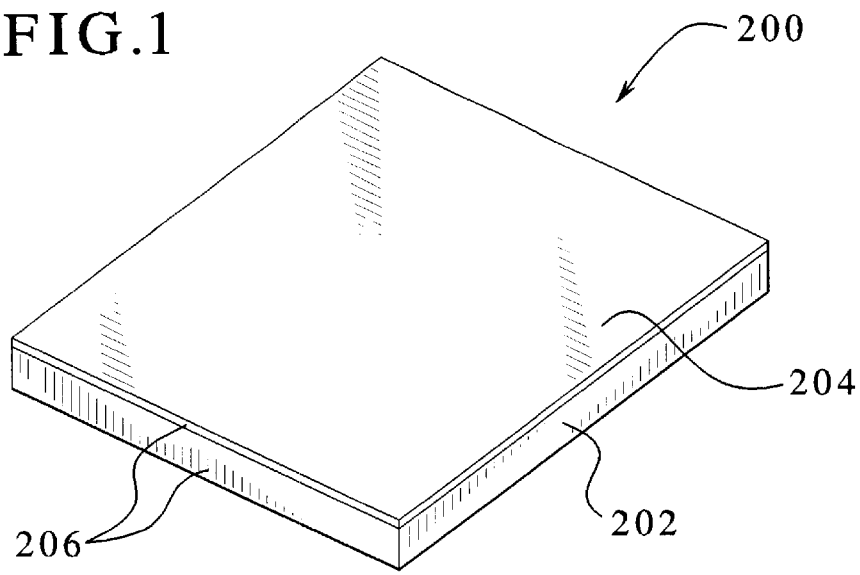
FIG. 1 is a perspective view of a coextruded multilayered film.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Referring to the drawings, it will be understood that the drawings have generally been enlarged (i.e., not to scale) for clarity and illustration purposes. FIG. 1 shows a multilayer film generally designated with the reference numeral 200. The film 200 is a coextruded film. The film 200 has a first layer 202 that can be preferably selected from polymeric materials and more preferably from polyolefins, polyamides, polyesters, polymer blends and the like. In a preferred form, the first layer 202 is a polyolefin blend of SEBS, polypropylene and ethylene vinyl acetate. This blend is described in greater detail in U.S. Pat. No. 4,140,162, which is incorporated herein by reference and made a part hereof. The polyolefin blend is sold by Baxter International Inc., the assignee of the present invention, under the trademark PL-732®.

The second layer 204 can be preferably selected from polymeric materials and especially those that do not readily seal well to themselves or other polymers. More preferably, the second layer is a polyamide, SEBS copolymer, ethylene vinyl alcohol copolymer or polystyrene. In a preferred form of the invention, the second layer 204 is a polystyrene. The second layer 204 covers the first layer 202 wherein their respective peripheral edges 206 are in registration.

Figure 2:
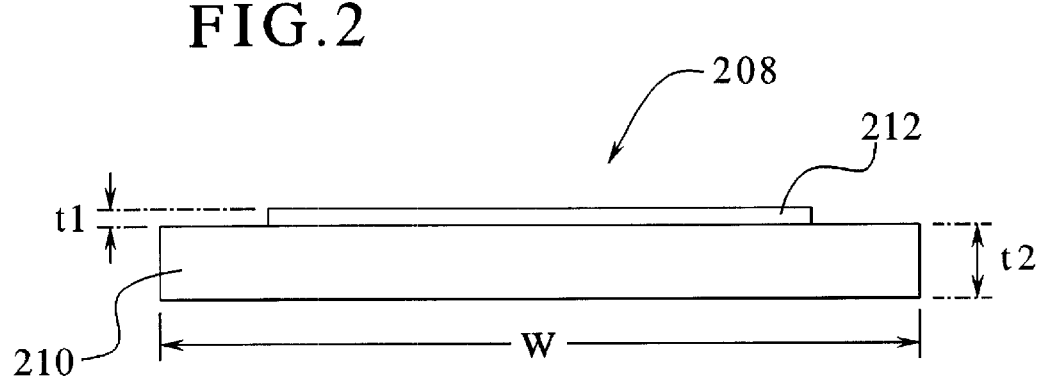
FIG. 2 is an end elevational view of another type of multilayered film.

FIG. 2 shows another embodiment of a multilayer film 208. This film 208 is the same as the film shown in FIG. 1 with the exception that it is not coextruded but is "built-up." The film 208 has a first layer 210 and a second layer 212. The second layer 212 is placed on top of the first layer 210 and adhered to the first layer 210 by welding or other means for sealing known in the art. Thus, the film 208 is built-up by stacking the layers, one on top of another. In addition, the second layer 212 has a smaller width than the width of the first layer 210 and is centrally disposed on the first layer 210. The first layer 210 has a first thickness t1 and the second layer 212 has a second thickness t2. The film 210 thus has a stepped configuration wherein the overall thickness of the film 210 varies across the width W of the film. It is understood that additional layers could be stacked on the second layer 212 if desired. For example, it is understood that the second layer 212 itself could be composed of a coextruded film having a PL-732® layer and a polystyrene layer such as shown in FIG. 1. The PL-732® layer could then be bonded to the first layer 210 (also PL-732®).

Figure 3:
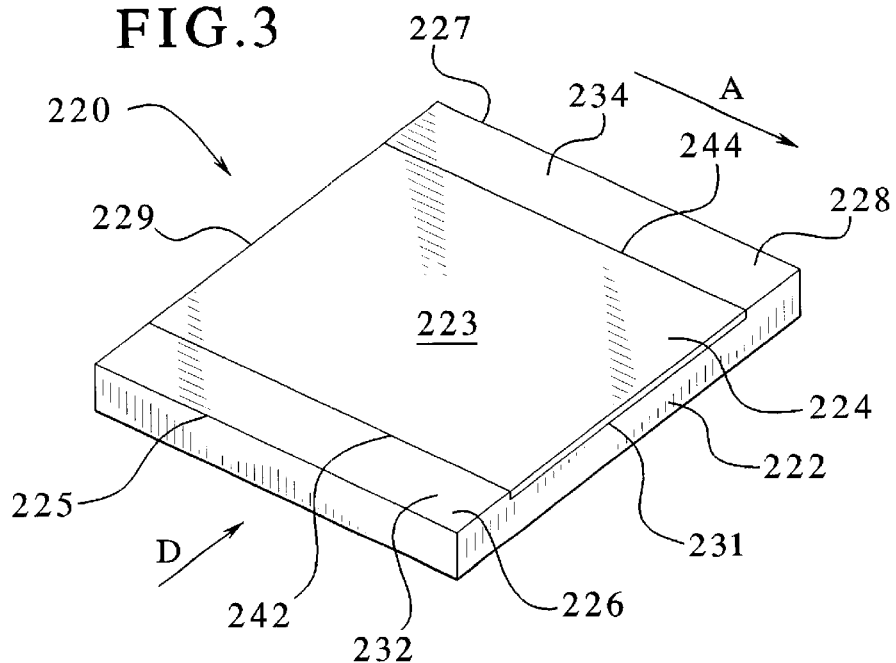
FIG. 3 is a perspective view of a coextruded multilayered film of the present invention.
Figure 4:
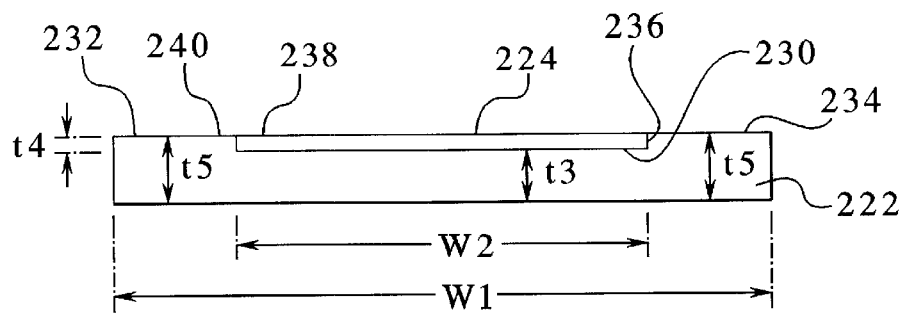
FIG. 4 is an end elevational view of the film of FIG. 3.

FIGS. 3 and 4 disclose a multilayer film of the present invention generally designated with the reference numeral 220. The film 220, sometimes referred to as a web, generally comprises a first layer 222 and a second layer 224. The material selections for the first layer 222 and the second layer 224 are respectively similar to the material selections for the films 200,208 of FIGS. 1 and 2. The width W1 of the first layer 222 is greater than the width W2 of the second layer 224 (FIG. 4). The first layer 222 defines a first lateral peripheral edge 225 and a second lateral peripheral edge 227. The first layer 222 also defines a first longitudinal peripheral edge 229 and a second longitudinal peripheral edge 231. Also, the second layer 224 is preferably centrally disposed on the first layer 222 within the first lateral peripheral edge 225 and the second lateral peripheral edge 227 of the first layer 222. The second layer 224 thus forms a "stripe" 223 along the film 220. The "stripe" extends in a lateral direction parallel to the lateral peripheral edges 225, 227 (also referred to as the machine direction, to be described in greater detail below) designated by the arrow A from the first longitudinal peripheral edge 229 to the second longitudinal peripheral edge 231. Accordingly, the present invention provides a "striped" film that is a non-continuous multilayer structure, as viewed in a direction perpendicular to the machine direction A. Striping is the process of coextruding a non-continuous multilayer structure (as viewed perpendicular to the machine direction). In other words, when viewing the film 220 in a direction D perpendicular to the machine direction A and in the same plane (FIG. 3), the film 220 is noncontinuous by having a first layer section 226, adjacent the stripe 223, adjacent another first layer section 228.

As further shown in FIGS. 3 and 4, the second layer 224 is positioned on the first layer 222 to define an overlap area 230. As the stripe 223 composed of the second layer 224 is positioned within the lateral peripheral edges 225,227 of the first layer 222, the first layer 222 has a first flange 232 at the first lateral peripheral edge 225 and a second flange 234 at the second lateral peripheral edge 227. The first and second flanges 232,234 are formed from the first layer material. The second layer 224 is positioned between the flanges 232,234 and extend from the first longitudinal peripheral edge 229 to the second longitudinal peripheral edge 231. The flanges 232,234 extend in a lateral direction parallel with the machine direction A.

At the overlap area 230, the first layer 222 has a thickness t3. The second layer 224 has a thickness t4. At the flanges 232,234, the first layer 222 has a thickness t5. The thickness t5 corresponds to the sum of the thicknesses t3 and t4. While the thickness of the film 220 may have very minute thickness variations such as ±0.002 in. to 0.003 in. across the width W1 of the film, the thickness of the film 220 is considered to be substantially uniform across the width W1 of the web, or film 220. Thus, the thickness of the film 220 generally corresponds to a thickness equal to thickness t5. The thickness t5 can generally be in the range of 0.006 in.–0.012 in. and most preferably the thickness t5 is approximately 0.008 in.–0.010 in. The thickness t4 can generally be in the range of 0.0003 in.–0.003 in. and most preferably the thickness t4 is approximately 0.0003 in. –0.001 in. The thickness t3 can generally be in the range of 0.0057 in.–0.009 in.

As further shown in FIGS. 3 and 4, the first layer 222 has a channel 236 positioned between the flanges 232,234 and extending parallel to the flanges 232,234 in the machine direction A. The second layer 224 is positioned in the channel 236. In a preferred form of the invention, the second layer 224 fills the channel 236 wherein an upper surface 238 of the second layer is level, or substantially flush, with an upper surface 240 of the flanges 232,234. This assures that the film 220 has a substantially uniform thickness across the width W1 of the film. In addition, the second layer has a first lateral edge 242 that contacts the first flange 232 and a second lateral edge 244 that contacts the second flange 234.

Figure 8:
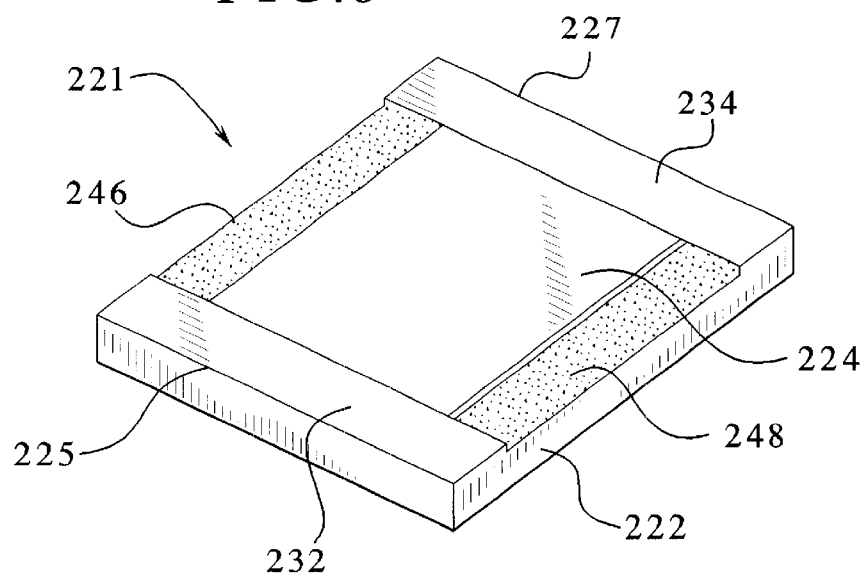
FIG. 8 is a perspective view of the film of FIG. 3 having a portion of opposite longitudinal peripheral edges stripped.

As shown in FIG. 8, a film corresponding to the film 220 can be modified to a film 221 having "stripped" portions. The stripped film 221 has portions of the second layer 224 removed at the first longitudinal peripheral edge 229 and the second longitudinal peripheral edge 231, or stripped, thus exposing portions of the channel 236. These stripped portions define a first longitudinal segment 246 and a second longitudinal segment 248. Thus, the modified film 221 is both "striped" and "stripped." This modified film 221 will be described in greater detail below.

The film 220 is constructed by a coextrusion process called "striping." Striping is the process of coextruding a non-continuous multilayer structure (as viewed perpendicular to the machine direction). The coextrusion process is performed using a multi-manifold as is known in the art. As also known in the art, one of the manifolds is interrupted causing a noncontinuous web of material applied to the bottom web of material. The bottom layer (corresponding to the first layer 222) of material is sometimes referred to as the substrate material. In the preferred embodiment of the invention such as the film 220, the multi-manifold extrudes the second layer 224 of polystyrene over the wider first layer 222, thus forming the striped film 220. The second layer 224 displaces a central portion of the first layer at the overlap area 236 wherein the film 220 has a substantially uniform thickness across the width W1 of the film 220.

Figure 5:
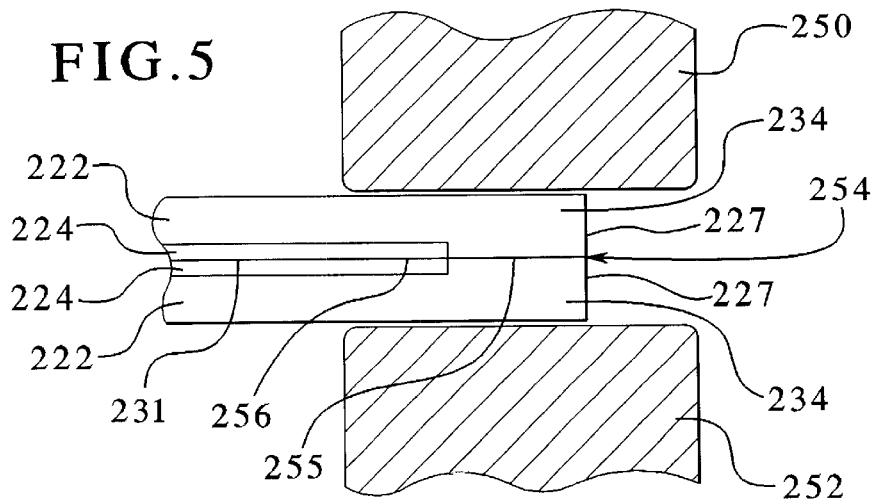
FIG. 5 is a partial cross-sectional view showing a pair of films shown in FIG. 3 positioned in confronting relation wherein outer peripheral edges of the films are positioned between a pair of open welding dies.
Figure 6:
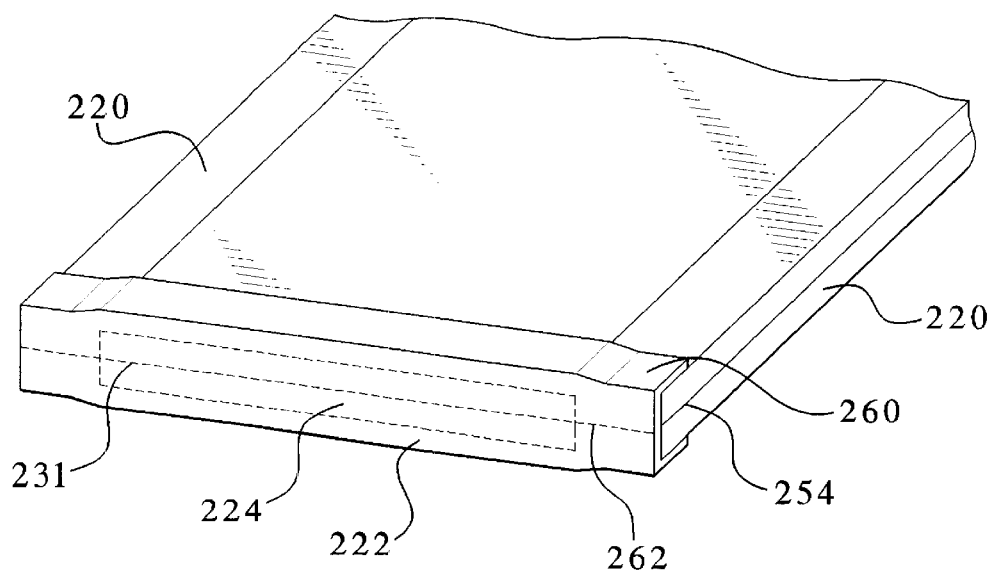
FIG. 6 is a partial perspective view showing one side of a container made from films of the present invention having an encapsulated seam.

Another aspect of the present invention is a container suitable for medical uses constructed from the film 220. The film 220 can be formed into a container by placing a pair of films 220 in overlapping relation and bonding the inner surfaces of their outer peripheries to define a chamber or pouch. A single sheet of film 220 could also be folded to form a container. FIG. 5 shows a pair of films 220 in overlapping relation between a pair of opened welding dies 250,252. The peripheral edges of the films 220 are in registration wherein the respective second lateral peripheral edges 227 of the films 220 are shown. The dies 250,252 are closed to compress the films 220 and sealing energies are delivered through the dies 250,252 to form a peripheral seam 254 at the outer periphery of the films 220. As further shown in FIG. 5, the seam 254 can be of a width to include a portion of the second layers 224. The seam 254 has an outer portion 255 and an inner portion 256. The first layers 222 of the films 220 are sealed together at the flanges 234 forming the outer portion 255 of the seam 254. The outer portion 255 of the seam 254 is a strong bond as both of the flanges 234 are made from a material such as PL-732® which bonds to itself well. The inner portion 256 of the seam 254 includes the second layers 224 bonded to one another. The inner portion 256 is not as strong because the second layers 224 are made from a material such as polystyrene which does not bond to itself very well. As previously discussed, the second layers 224 extend from the first longitudinal peripheral edge 229 to the second longitudinal peripheral edge 231. FIG. 5 shows the second layers 224 extending to the second longitudinal peripheral edges 231 of the films 220. Because the second layers 224 are made from a material which does not bond well to itself, the portion of the seam 254 formed at the longitudinal peripheral edges 229,231 are typically reinforced, or encapsulated as disclosed in commonly-assigned, copending Application Ser. No. 08/998,256. As shown in FIG. 6, a skirt 260 is placed over a portion 262 of the seam 254 at the longitudinal peripheral edges 231 to encapsulate this portion 262 of the seam 254. The longitudinal peripheral edges 231 are normal to the machine direction A.

Figure 10:
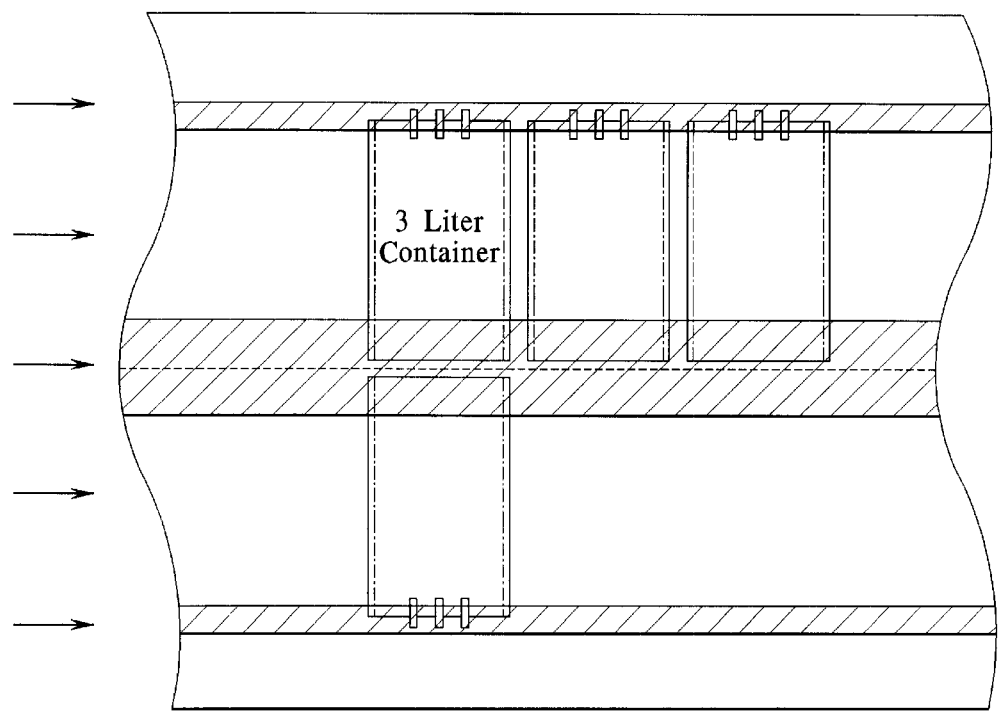
FIG. 10 is a partial plan view of an assembly line for manufacturing containers of the present invention.

FIG. 7 shows a container 264 constructed from a pair of the films 220. It will be understood that the films 220 have different dimensions than the films 220 shown in FIGS. 3–6. The container 264 has a first wall 265 composed of the film 220 and a second wall 267 composed of the film 220. The respective first lateral peripheral edges 225 and second lateral peripheral edges 227 extend in the machine direction A. The respective first and second longitudinal peripheral edges 229,231 extend in a direction perpendicular to the machine direction A. As further shown, the respective flanges 232,234 extend in a direction parallel to the machine direction A. It is understood that the seam 254 extends around the full periphery of the container 264. The portion of the seam 254 formed at the flanges 232,234 accommodate ports 266 and tail features such as labels and hangers 268 prior to forming the seam 254. This is typical since these ends are the free ends as the films 220 are dispensed from roll stock during the manufacturing process of the bags. The respective longitudinal peripheral edges 229,231 are sealed forming the portions 262 of the seam 254. As discussed, these portions 262 of the seam 254 are not as strong and, therefore, the portions 262 are reinforced with the skirts 260. A first skirt 260 connects an outer side of the first wall 265 at the first longitudinal peripheral edge 229 to an outer side of the second wall 267 at the first longitudinal peripheral edge 229 to encapsulate a first longitudinal portion 262a of the seam 254. A second skirt 261 connects an outer side of the first wall 265 at the second longitudinal peripheral edge 231 to an outer side of the second wall 267 at the second longitudinal peripheral edge to encapsulate a second lateral portion 262b of the seam 254. FIG. 10 shows a schematic view of an assembly line constructing the containers 264.

As previously stated, the second layer 224 is preferably composed of a polystyrene. When the films 220 are constructed into the container 264, the second layer 224 corresponds to the inner layer of the container 264. Accordingly, in one preferred form of the invention, the second layer 224 defines an inner cell growth surface wherein the container 264 functions as a cell culture container.

Figure 9:
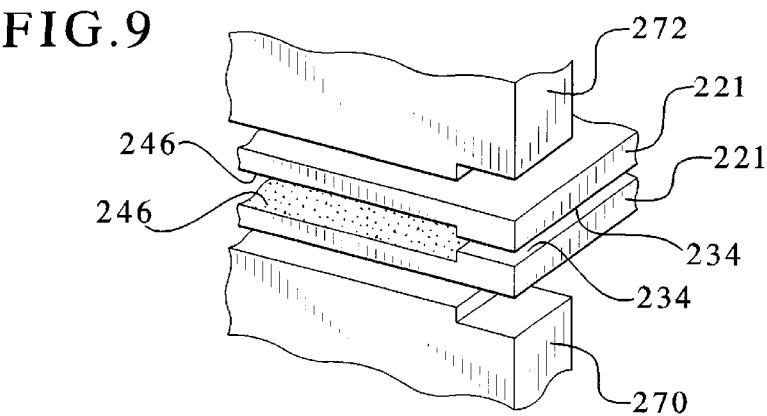
FIG. 9 is a partial cross-sectional view showing a pair of films shown in FIG. 8 positioned in confronting relation wherein the stripped longitudinal peripheral edges of the films are positioned between a pair of open, stepped welding dies.

As previously discussed, FIG. 8 shows the modified film 221 that is both striped and stripped. A pair of modified films 221 can be formed into a container. The portions of the striped second layer 224 are stripped to define the first longitudinal segment 246 at the first longitudinal peripheral edge 229 and the second longitudinal segment 248 at the second longitudinal peripheral edge 231. Therefore, the first layer 222 is exposed at the lateral segments 246,248. Thus, the material of the first layer 222 is exposed on all peripheral edges 225,227,229,231 of the film 221. As discussed, this material bonds well to itself and, therefore, strong seams can be formed on all peripheral edges of the container without reinforcing the seam by encapsulating or other method or structure. When a pair of films 221 are placed in confronting relation to form a container, the first and second longitudinal segments are respectively sealed together to define longitudinal portions of the seam. Also, when a pair of films 221 are placed in confronting relation to form a container, the differences in thicknesses of the first layer 222 at the flanges 232,234 and the longitudinal segments 246,248 must be accounted for by the welding dies. Thus, it is desirable to form the peripheral seams at these edges of containers formed from the modified films 221 using the isocompression sealing process described in parent patent application Ser. No. 09/016,236 (which has been incorporated herein by reference) using stepped dies. FIG. 9 shows a schematic view of a set of stepped dies 270,272 used to seal a pair of modified films 221 at a pair of first longitudinal segments 246. The dies 270,272 are stepped to accommodate the different thicknesses of the confronting flanges 232,234 and confronting longitudinal segments 246,248. By using the isocompression method, the seam 254 is formed between the dies 270,272, wherein the first layers 222 at the longitudinal segments 246 are compressed to a first compression ratio and the first layers 222 at the lateral peripheral edges 225,227 (or flanges 232,234) are compressed to a second compression ratio. The dies 270,272 are designed so that the first compression ratio is substantially equal to the second compression ratio.

Thus, the present invention provides for a multilayer film capable of forming a strong seal at its peripheral edges to form a container, while not requiring an inner layer capable of forming a strong seal. When forming a container using the striped film 220, therefore, the need to encapsulate all four peripheral edges of the container using a skirt is eliminated. Because of the stripe of the second layer 224, the flanges 232,234 of the first layer 222 are exposed. This allows the facing surfaces of the flanges 232,234 to be bonded together using conventional methods. Because the need for encapsulation is reduced to only two sides of the container, the encapsulation process is much more automation friendly. This leads to a more consistent product at a lower cost. Also, the modified film 221 that is "striped" and "stripped" can be used to form a container eliminating the need for any encapsulation. Additionally, the striped film 220 of the present invention permits the inclusion of ports of a material that is incompatible with the inner surfaces (second layer 224) of the container so long as the port material is compatible with the first layer 222 material.

It is understood that, given the above description of the embodiments of the invention, various modifications may be made by one skilled in the art. Such modifications are intended to be encompassed by the claims below.

What is claimed is:

1. A multilayered film suitable for medical uses, the film being coextruded in a lateral machine direction, the film comprising:

a first layer defining a pair of peripheral edges extending in the lateral direction; and a second layer coextruded onto the first layer, the second layer positioned within the peripheral edges defining a stripe along the film, wherein the film has a width and a thickness wherein the thickness of the film is substantially uniform across the entire width of the film.

2. The film of claim 1 wherein the film has a width and a thickness wherein the thickness of the film is substantially uniform across the width of the film.

3. The film of claim 1 wherein the first layer is composed of a polyolefin.

4. The film of claim 1 wherein the second layer is composed of a polystyrene.

5. The film of claim 1 wherein the first layer has a first flange and a second flange, the flanges extending in the lateral direction, the second layer being positioned between the flanges.

6. The film of claim 5 wherein the first layer has a channel positioned between the flanges and extending parallel to the flanges, the second layer positioned in the channel.

7. The film of claim 6 wherein the second layer positioned in the channel defines an overlap area wherein the second layer has a thickness in the range of 0.0003 in. to 0.003 in., and the first layer has a thickness in the range of 0.006 in. to 0.012 in. at the flanges and the first layer has a thickness in the range of 0.0057 in. to 0.009 in. at the overlap area.

8. The film of claim 1 wherein the thickness of the film is approximately 0.006 in. to 0.010 in.

9. The film of claim 1 wherein the second layer defines an inner cell growth surface.

10. The film of claim 1 wherein when viewed from a direction perpendicular to the lateral direction and in the same plane, the film is noncontinuous by having a first layer section adjacent the stripe of the second layer adjacent another first layer section.

11. The film of claim 1 wherein the second layer has a first longitudinal portion removed to define a first longitudinal segment on the first layer, and the second layer has a second longitudinal portion removed to define a second longitudinal segment on the first layer.

12. A multilayered film suitable for medical uses comprising:

a first layer having a first flange and a second flange, the first flange and the second flange extending in a lateral direction, the first layer having a channel positioned between the first flange and the second flange and extending parallel thereto; and a second layer positioned in the channel wherein the film has a substantially uniform thickness across an entire width of the film.

13. The film of claim 12 wherein the first layer is composed of a polyolefin.

14. The film of claim 12 wherein the second layer is composed of a polystyrene.

15. The film of claim 12 wherein the second layer has a first lateral edge and a second lateral edge, the first lateral edge contacting the first flange and the second lateral edge contacting the second flange.

16. The film of claim 12 wherein the second layer has a first longitudinal portion removed to define a first longitudinal segment on the first layer, and the second layer has a second longitudinal portion removed to define a second longitudinal segment on the first layer.

17. A coextruded multilayered film suitable for medical uses comprising:

a first layer comprising a polyolefin, the first layer having a first flange and a second flange, the first flange and second flange extending in a lateral direction, the first layer having a channel positioned between the first flange and the second flange and extending parallel thereto; and a second layer comprising polystyrene and positioned in the channel wherein the film has a substantially uniform thickness across an entire width of the film.

18. A container suitable for medical uses comprising:

a first wall having a first layer defining a first lateral peripheral edge and a second lateral peripheral edge and a first longitudinal peripheral edge and a second longitudinal peripheral edge, and a second layer adhered to the first layer, the second layer positioned within the lateral peripheral edges defining a stripe, the stripe extending from the first longitudinal peripheral edge to the second longitudinal peripheral edge, wherein the first wall has a substantially uniform thickness across an entire width of the film;

a second wall having a first layer defining a first lateral peripheral edge and a second lateral peripheral edge and a first longitudinal peripheral edge and a second longitudinal peripheral edge, and a second layer adhered to the first layer, the second layer positioned within the lateral peripheral edges defining a stripe, the stripe extending from the first longitudinal peripheral edge to the second longitudinal peripheral edge; and a seam attaching the first and second lateral peripheral edges and the first and second longitudinal peripheral edges of the first wall and the second wall.

19. The container of claim 18 further comprising:

a first skirt connecting an outer side of the first wall at the first longitudinal peripheral edge to an outer side of the second wall at the first longitudinal peripheral edge to encapsulate a first portion of the seam; and a second skirt connecting an outer side of the first wall at the second longitudinal peripheral edge to an outer side of the second wall at the second longitudinal peripheral edge to encapsulate a second portion of the seam.

20. The container of claim 18 wherein the second layer of the first wall has a first longitudinal portion removed at the first longitudinal peripheral edge to define a first longitudinal segment on the first layer, and the second layer has a second longitudinal portion removed at the second longitudinal peripheral edge to define a second longitudinal segment on the first layer, and the second layer of the second wall has a first longitudinal portion removed at the first longitudinal peripheral edge to define a first longitudinal segment on the first layer, and the second layer has a second longitudinal portion removed at the second longitudinal peripheral edge to define a second longitudinal segment on the first layer, wherein the first longitudinal segments of the walls are sealed together and the second longitudinal segments of the walls are sealed together to define longitudinal portions of the seam.

21. The container of claim 18 further comprising:

an access port extending through the seam at the lateral peripheral edges of the walls to define a fluid pathway.

22. The container of claim 18 wherein the seam at the lateral peripheral edges has an inner portion wherein the second layer of the first wall and the second layer of the second wall are sealed together and the seam has an outer portion wherein the first layer of the first wall and the first layer of the second wall are sealed together.

23. The container of claim 20 wherein the seam is formed by compressing the walls between welding dies, wherein first layers of the walls at the longitudinal segments are compressed to a first compression ratio and the first layers of the walls at the lateral peripheral edges are compressed to a second compression ratio, the first compression ratio being substantially equal to the second compression ratio.

24. A multilayered film suitable for medical uses, the film comprising:

a first layer defining a pair of peripheral edges, the first layer having a channel positioned between the peripheral edges and extending parallel thereto; and a second layer coextruded onto the first layer and adhered thereto, the second layer positioned in the channel wherein the film has a substantially uniform thickness across an entire width of the film.

25. A multilayered film suitable for medical uses, the film being coextruded in a lateral machine direction, the film comprising:

a first layer having a first flange and a second flange, the flanges extending in the lateral direction and defining a pair of peripheral edges, the first layer further having a channel positioned between the flanges and extending generally parallel to the flanges; and a second layer adhered to the first layer, the second layer positioned in the channel and within the peripheral edges defining a stripe along the film, wherein the film has a substantially uniform thickness across an entire width of the film.

26. A container suitable for medical uses comprising:

a first wall having a first layer having a first flange and a second flange, the first layer having a channel positioned between the first flange and the second flange and extending parallel thereto, and a second layer positioned in the channel wherein the film has a substantially uniform thickness across an entire width of the first wall;

a second wall having a first layer having a first flange and a second flange, the first layer having a channel positioned between the first flange and the second flange and extending parallel thereto, and a second layer positioned in the channel wherein the film has a substantially uniform thickness across an entire width of the second wall; and a seam attaching respective peripheral edges of the first wall and the second wall.

* * * * *